(12) United States Patent
Friedler et al.

(10) Patent No.: US 6,664,368 B1
(45) Date of Patent: Dec. 16, 2003

(54) INHIBITION OF NUCLEAR IMPORT BY BACKBONE CYCLIC PEPTIDE ANALOGS

(75) Inventors: Assaf Friedler, Jerusalem (IL); Abraham Loyter, Jerusalem (IL); Chaim Gilon, Jerusalem (IL); Amnon Wolf, Herzlia (IL)

(73) Assignees: Yissum Research Development Co. of the Hebrew University of Jerusalem, Jerusalem (IL); Peptor Ltd., Rehovot (IL)

( * ) Notice: Subject to any disclaimer, the term of this patent is extended or adjusted under 35 U.S.C. 154(b) by 0 days.

(21) Appl. No.: 09/564,677

(22) Filed: May 4, 2000

Related U.S. Application Data (63) Continuation of application No. PCT/IL98/00577, filed on Nov. 26, 1998.

(30) Foreign Application Priority Data

Nov. 27, 1997 (IL) .................................. 122343

(51) Int. Cl.$^7$ .................................. C07K 7/50
(52) U.S. Cl. ............... 530/317; 530/330; 530/332; 514/11; 514/17
(58) Field of Search ............... 530/317, 330, 530/332; 514/11, 17

(56) References Cited

U.S. PATENT DOCUMENTS 5,723,575 A    3/1998   Gilon et al. ............... 530/317

OTHER PUBLICATIONS

Friedler, Biochemistry 37, 5616–5622, 1998.*
Shi Molecular and Cellular Biology 12, 2186–92, 1992.*
Imamoto J. Cell. Biol. 119, 1047, 1992.*
Lehninger Biochemistry, pp. 1002–1003, Worth Publishers, 1975.*
Lin J. Biol. Chem. 270, 14255, 1995.*
Mattaj, Annual Review of Biochemistry 67, 265–306, 1998.*
Steinkasserer Journal of Virology 69 (2) 814–24, 1995.*
Traber Antiviral Chem Chemother 5, 331–339, 1994.*
Dorfman Journal of Virology 70 (9) 5751–7, 1996.*
Fouchier, EMBO Journal 16, 4531, 1997.
Gulizia, J. Virol. 68 2021, 1994.
Hibbard, J. Virol. 69, 4656, 1995.

* cited by examiner

*Primary Examiner*—Christopher S. F. Low
*Assistant Examiner*—David Lukton
(74) *Attorney, Agent, or Firm*—Winston & Strawn

(57) ABSTRACT

The design and the synthesis of backbone cyclic peptide analogs which functionally mimic the nuclear localization signal (NLS) region of macromolecules is disclosed. The principles of the invention are exemplified for the NLS sequences of the human immunodeficiency virus type 1 proteins MA, Vpr, Tat and NLS-like sequences of HIV-1 protein Vif. We disclose the discovery of a novel, highly potent backbone cyclic peptide, designated BCvir, which inhibits nuclear import with an IC$_{50}$ value of 35 nM. This inhibitory potency is to be compared to 12 $\mu$M exhibited by the linear parent HIV-1 MA NLS peptide. BCvir also reduced HIV-1 production by 75% in infected non-dividing cultured human T-cells and was relatively resistant to tryptic digestion. These properties render backbone cyclic peptide analogs of NLS or NLS-like sequences as candidates for novel drugs based on blocking nuclear import of viral genomes.

30 Claims, 5 Drawing Sheets

| peptide No. | atoms in ring | n | m |
|---|---|---|---|
| 1 | 18 | 0 | 2 |
| 2 | 19 | 0 | 3 |
| 3 | 20 | 0 | 4 |
| 4 | 20 | 2 | 2 |
| 5 | 21 | 0 | 5 |
| 6 | 21 | 2 | 3 |
| 7 | 21 | 3 | 2 |
| 8 | 22 | 2 | 4 |
| 9 | 22 | 3 | 3 |
| 10 | 22 | 4 | 2 |
| 11 | 23 | 2 | 5 |
| 12 | 23 | 3 | 4 |
| 13 | 23 | 4 | 3 |
| 14 | 24 | 3 | 5 |
| 15 | 24 | 4 | 4 |
| 16 | 24 | 6 | 2 |
| 17 | 25 | 4 | 5 |
| 18 | 25 | 6 | 3 |
| 19 | 26 | 6 | 4 |
| 20 | 27 | 6 | 5 |

(b)

| Peptide No. | AA | AA$_2$ |
|---|---|---|
| 19.1 | Ser | Gly |
| 19.2 | Leu | Gly |
| 19.3 | Met | Gly |
| 19.4 | ---- | Gly |
| 21* | Leu | Cys |
| 22* | Leu | Val |

*These two peptides were synthesized after screening of the second library, to improve its inhibitory activity

INHIBITION OF NUCLEAR IMPORT BY BACKBONE CYCLIC PEPTIDE ANALOGS

This application is a continuation of PCT application No. PCT/IL98/00577, filed Nov. 26, 1998, which claims priority to Israeli application No. 122343, filed Nov. 27, 1997

FIELD OF THE INVENTION

The present invention concerns the modulation of transfer of macromolecules from the cell cytoplasm to the cell nucleus, to backbone cyclic peptides which inhibit nuclear import and to compositions and methods using these peptides to inhibit nuclear localization and virus production.

BACKGROUND OF THE INVENTION

The life cycle of eukaryotic cells depends upon translocation of functional proteins from the cytoplasm into the cell nucleus in which DNA replication and RNA biosynthesis occurs. Also, nucleo-cytoplasmic transport of viral genomes is essential for the replication and assembly of many animal viruses. For example, the nuclear import of Human immunodeficiency virus (HIV-1), and of Herpes simples virus (HSV), is crucial for the productive infection of non-dividing cells (Von-Schwedler, et al.(1994), *Proc.Natl.Acad.Sci. USA* 91, 6992–6996), in which the nuclear membrane is intact.

The Nucear Localization Signal (NLS) is a transport signal within proteins which mediates their nuclear uptake by a complex mechanism (Melchior (1995) *Curr.Opin.Cell.Biol.* 7, 310–318 Garcia-Bustos, et al. (1991) *Biochim. Biophys. acta* 1071, 83–101). It has a semi-consensus sequence generally composed of 5–15 amino acid residues, of which a significant proportion are positively charged (lysine and arginine) (Dingwall, and Laskey (1991) *TIBS* 16, 478–481). Nuclear import is initiated in the cytoplasm by specific binding of the NLS to a cytoplasmic receptor, generally designated as an NLS-binding protein (NBP). A number of proteins that interact with NLS sequences nave been detected, identifying them as nuclear import receptors (Nigg, (1997) *Nature* 386, 779–787). The first nuclear import pathway that was discovered operates with the karyopherin heterodimer also known as importin (Gorlich et. al. (1995) *Nature* 377, 246–248).

Viral transport into the nucleus is made possible as their genomes are complexed with viral proteins that harbor unique NLS's crucial for nuclear transport. At least three HIV-1 proteins are involved in nuclear import of the viral preintegration complex (PIC), thus displaying partially redundant nuclear localization activity: The HIV-1 MA, a nucleocapsid component (Bukrinsky et. al. *ibid*), the auxiliary protein Vpr (Heinzinger et. al. (1994) Proc. Natl. Acad. Sci. USA 91, 73 11–7315), and the viral integrase (Gallay et. al. (1997) Proc. Natl. Acad.Sci. USA 94, 9825–9830). HIV-1 also expresses several auxiliary proteins of molecular weight under 30 kDa (Miller and Sarver, (1997) Nature Medicine 3, 389–394). Out of these proteins Tat, Rev, Nef and Vif contain NLS-like sequences and accumulate, under certain conditions, within the nuclei of infected cells. It has recently been reported that Vpr (Karni et. al.(1998) FEBS Lett. 429, 421–425), Tat (Efthymiadis et. al. (1998) J Biol Chem 273, 1623–1628) and Rev (Henderson and Percipalle, (1997) J Mol Biol 274, 693–707) promote nuclear import by a distinct non-importin pathway. Linear peptides derived from NLS sequences function as an active NLS since their covalent conjugation to BSA caused nuclear import of the resulting conjugate (Bukrinsky, et al. ibid; Goldfarb, et al. (1986) Nature 322, 641–644). Such peptides also inhibit nuclear import as was demonstrated by inhibition of the HIV-1 matrix protein (MA) and its preintegration complex (Gulizia, et al. (1994) *J. Virol.* 68, 2021–2025). However, due to their structural flexibility and metabolic instability, the therapeutic use of linear NLS peptides as anti viral drugs is impractical.

Proteinomimetics are small molecules that mimic the structure and/or the activity of a large parent protein. The availability of such small molecules can be useful for the detailed study of the biological function, molecular structure and folding of proteins. Moreover, proteinomimetics are excellent candidates for becoming a novel type of drugs, since they overcome some of the limitations that currently hamper the therapeutic use of proteins and polypeptides such as antigenicity, metabolic instability and poor bioavailability. While many structural proteinomimetics have already been described, most of them were deprived of the biological function which characterized the parent protein. Also attempts to obtain small peptides which mimic catalytic sites of enzymes and preserve their enzymatic activity have so far failed (Corey, and Corey (1996) *Proc.Natl.Acad.Sci. USA* 93, 11428–11434). Very few examples of structural proteinomimetics which retain the biological activity and resemble the structure of the corresponding proteins have so far been disclosed, such as the zinc-finger (Struthers, et al. (1996) *Science* 271, 342–345) and the metal-binding proteinomimetics (Robertson, et al. (1994) *Nature* 368, 425–432; Pessi, et al. (1993) *Nature* 362, 367–369). We now disclose a general approach for the design and synthesis of small backbone cyclic peptides which mimic structure and the function of active regions in proteins.

Backbone cyclization is a general method by which a conformational constraint is imposed on peptides through the connection of the $N^\alpha$ or $C^\alpha$ atoms in the peptide backbone to each other or to side chains or to the carboxyl and amino termini (Gilon et al. (1991) *Biopolymers* 31, 745–750). Backbone cyclization has been previously shown to convert peptides into selective and metabolically-stable peptidomimetics with enhanced biological activity as compared to the linear parent peptide as discussed for instance in EPO 564,739 A2 and WO 95/33765; Byk, et al. (1996) *J. Med. Chem.* 39, 3174; Bitan, et al. (1997) *J. Pept. Res.* 49, 421). Cycloscan is a selection method based on conformationally constrained backbone cyclic peptide libraries that allows rapid detection of the most active backbone cyclic peptide derived from a given sequence as disclosed in WO 97/09344. The diversity of cycloscan, which includes modes of backbone cyclization, ring position, ring size and ring chemistry allows the Generation of a large number of sequentially biased peptides that differ solely by their conformation in a gradual discrete manner. The principles of the "backbone cyclic proteinomimetic" approach are based on the following, steps: (i) elucidation of the active residues in the target protein (ii) design and modeling of an ensemble of prototypic backbone cyclic peptides that encompass the active residues and their conformation resemble that of the parent protein (iii) cycloscan of each backbone cyclic prototype until a lead compound is discovered (iv) structural analysis of the best lead and (v) optimization through iteration.

SUMMARY OF THE INVENTION

It is one object of the present invention to provide backbone cyclic peptide analogs which mimic Nuclear Localization Signal (NLS) regions in macromolecules. It is another object of the invention to utilize the backbone cyclic peptide analogs to inhibit nuclear import of NLS containing macromolecules into the cell nucleus. It is yet another object of the invention to provide backbone cyclic peptide analogs which mimic the NLS region of various proteins of the human immunodeficiency virus. Yet another object of the present invention to provide compositions and methods of using said backbone cyclic peptides to inhibit virus replication in infected cells. According to the principles of the present invention it is now disclosed that using the backbone cyclic proteinomimetic approach it is possible to design libraries of backbone cyclic peptides that mimic the region of the NLS sequence. These libraries can be used to identify molecules which can then be further optimized and refined to mimic the specific NLS sequences of particular macromolecules as required. These principles are exemplified using the NLS sequence of certain viral proteins. The backbone cyclic peptides obtained are useful to inhibit the translocation of macromolecules from the cell cytoplasm to the cell nucleus thereby disrupting the propagation of tile virus.

Currently more preferred embodiments according to the present invention include backbone cyclic peptide analogs which can mimic the action of NLS sequences and of NLS-like sequences of HIV-1. These preferred embodiments encompass backbone cyclic analogs of the NLS sequence selected from the HIV-1 viral proteins MA, Tat and Vpr.

Yet another preferred embodiment according of the present invention provides backbone cyclic analogs of a peptide within the HIV-1 protein Vif. These backbone cyclic peptides comprise analogs of residues 88 through 98 of Vif, having a short sequence of basic residues. This viral sequence inhibits but does not mediate nuclear import.

One currently most preferred embodiment of the present invention, is a backbone cyclic peptide analog of the general Formula I:

Formula I wherein n denotes an integer from 1 to 10 or may be zero, with the proviso that when n is zero NH is also absent; m denotes an integer from 1 to 10; R denotes lysine or glutamine; AA and AA2 independently denote an amino acid residue which may be the same or different.

A more preferred embodiment according to the present invention, is a backbone cyclic peptide analog of the general Formula II:

Formula II wherein n is an integer from 1 to 10 or may be zero, with the proviso that when n is zero NH is also absent; m is an integer from 1 to 10, and R denotes Lys or Gln.

A yet more preferred embodiment according to the present invention, is a backbone cyclic peptide analog of the general formula III:

Formula III wherein R denotes Lys or Gln, AA denotes an amino acid residue selected from the group consisting of serine, leucine or methionine, and AA2 denotes an amino acid residue selected from the group consisting of valine, glycine or cysteine.

A currently most preferred embodiment according to the present invention is the peptide of Formula III wherein R is Lysine, AA is Leucine and AA2 is Valine which is designated herein as BCvir.

Yet another most preferred embodiment according to the present invention comprises backbone cyclic peptide analogs of the general formula IV:

Formula IV wherein m and n are each independently an integer from 1 to 10.

Pharmaceutical compositions comprising, as an active ingredient a backbone cyclic peptide capable of mimicking the NLS sequence are disclosed and claimed.

Further disclosed are methods of inhibiting the translocation of macromolecules from the cell nucleus to the cell cytoplasm by contacting the cells with an effective amount of a backbone cyclized peptide which mimics the NLS sequence of said macromolecule. These are useful for the prevention or treatment of viral infection both in vitro or in vivo in an animal in need of such treatment. The utility of these methods is exemplified by inhibiting the replication of virus in virus infected cells.

DETAILED DESCRIPTION OF THE INVENTION

It is now disclosed that the backbone cyclic proteinomimetic approach has led to the discovery of backbone cyclic peptide analogs, which inhibit nuclear import of macromolecules from the cell cytoplasm into the cell nucleus, the macromolecules being of the kind which enter the nucleus by the mediation of a nuclear localization signal. In the specification and in the claims the term "macromolecule" may refer to a protein or to a complex containing one or more proteins together with additional molecules. For instance, the complex may comprise DNA or RNA in addition to the protein bearing the NLS sequence, or NLS-like sequences. Specifically, the complex may comprise viral genomes. In the specification and in the claims the term "backbone cyclic peptide analog" refers to a sequence of amino acid residues wherein at least one nitrogen or carbon of the peptide backbone is joined to another such nitrogen or carbon, to a side chain or to one of the termini of the peptide. Furthermore, one or more of the peptide bonds of the sequence may be reduced or substituted by a non-peptidic linkage.

The term "amino acid" refers to compounds which have an amino terminus and carboxy terminus, preferably in a 1,2- 1,3-, or 1,4- substitution pattern on a carbon backbone. α-Amino acids are most preferred, and include the 20 natural amino acids (which are L-amino acids except for glycine), which are found in proteins, the corresponding D-amino acids, the biosynthetically available amino acids which are not found in proteins (e.g., 4-hydroxy-proline, 5-hydroxy-lysine, citrulline, ornithine, canavanine, djenkolic acid, β-cyanolanine), and synthetically derived α-amino acids, such as amino-isobutyric acid, norleucine, norvaline, homocysteine and homoserine. β-Alanine and γ-amino butyric acid are examples of 1,3 and 1,4-amino acids, and many others are well known to the art. Statine-like isosteres (a dipeptide comprising two amino acids wherein the CONH linkage is replaced by a CHOH), hydroxyethylene isosteres (a dipeptide comprising two amino acids wherein the CONH linkage is replaced by a $CHOHCH_2$), reduced amide isosteres (a dipeptide comprising two amino acids wherein the CONH linkage is replaced by a $CH_2NH$ linkage) and thioamide isosteres (a dipeptide comprising two amino acids wherein the CONH linkage is replaced by a CSNH linkage) are also useful residues for this invention.

Backbone cyclization is a general method by which a conformational constraint is imposed on peptides through the connection of the $N^\alpha$ or $C^\alpha$ atoms in the peptide backbone to each other or to side chains or to the carboxyl and amino termini (Gilon et al. (1991) *Biopolymers* 31,745–750). Backbone cyclization has been previously shown to convert peptides into selective and metabolically-stable peptidomimetics with enhanced biological activity as compared to the linear parent peptide as discussed for instance in EPO 564,739 A2 and WO 95/33765.

"Cycloscan" is a selection method based on conformationally constrained backbone cyclic peptide libraries that allows rapid detection of the most active backbone cyclic peptide derived from a given sequence as disclosed in WO 97/09344. The teachings of those disclosures are incorporated herein in their entirety by way of reference. The diversity of cycloscan, which includes modes of backbone cyclization, ring position, ring size and ring chemistry allows the generation of a large number of sequentially biased peptides that differ solely by their conformation in a gradual discrete manner.

The principles of the "backbone cyclic proteinomimetic" approach are based on the following steps: (i) elucidation of the active residues in the target protein (ii) design and modeling of an ensemble of prototypic backbone cyclic peptides that encompass the active residues and their conformation resemble that of the parent protein (iii) cycloscan of each backbone cyclic prototype until a lead compound is discovered (iv) structural analysis of the best lead and (v) to optimization through iteration.

The ability of the backbone cyclic peptides to inhibit the transfer of macromolecules from the cytoplasm to the nucleus was demonstrated in the first aspect in a model system utilizing NLS-BSA in an in vitro assay system. In the second aspect, utilizing a functional assay, the ability of backbone cyclic peptides to prevent transfer of macromolecules to the cell nucleus was demonstrated and was found to reduce HIV-1 production in non-dividing infected cultured cells, apparently by blocking its MA-mediated nuclear uptake. Based on these results it is postulated that these novel backbone cyclic peptides mimic the NLS region of the HIV-1 MA protein.

Irrespective of the mechanism involved the novel backbone cyclized peptides which mimic NLS sequences of macromolecules are claimed as such, as pharmaceutical compositions comprising as an active ingredient a therapeutically effective amount of a backbone cyclic peptide which mimics the NLS sequence of a macromolecule and for their utility in inhibiting the transfer of macromolecules from the cytoplasm to the nucleus.

The methods of the present invention are exemplified herein using backbone cyclic peptides which mimic the NLS sequence of HIV-1 proteins MA, Tat and Vpr or mimic the sequence spanning residues 88–98 of Vif, which comprises an NLS like sequence having basic residues. The peptides disclosed are shown to inhibit the replication of virus in infected cells. The skilled artisan will appreciate that the following examples are merely illustrative and serve as non limitative exemplification of the principles of the present invention and that many variations and modifications are possible within the scope of the currently claimed invention as defined by the claims which follow.

Certain abbreviations are used herein to describe this invention and the manner of making and using it. For instance AAA refers to amino acid analysis; Boc refers to tert-butyloxycarbonyl; BSA refers to bovine serum albumin; Bzl refers to benzyl; DCM refers to dichloromethane; DIEA refers to ethyidiusopropylamine, DMF refers to dimethylformamide; DMSO refers to dimethylsulfoxide; DTT refers to dithiothreitol; EGTA refers to ethylene glycol-bis(β-aminoethyl ether)N,N,N',N'-tetraacetic acid; FCS; refers to fetal calf serum; Fmoc refers to 9-fluorenylmethyloxycarbonyl; HIV-1, refers to human immunodeficiency virus type 1; HOBt refers to N-hydroxybenzotriazole; $IC_{50}$ refers to inhibitory concentration at 50%; MA refers to matrix protein; MBHA refers to 4-methylbenzhydrylamine; NLS refers to nuclear localization signal; NMP refers to N-methylpyrrollidinone; NMR refers to nuclear magnetic resonance; pMeOBzl refers to p-methoxybenzyl; PMSF refers to phenylmethylsulfonyl fluoride; PyBroP refers to bromo-tris-pyrrollidino-phosphonium hexafluorophosphate; SMPS refers to simultaneous multiple peptide synthesis; SPPS refers to solid phase peptide synthesis; TBTU refers to 2-(1-hydroxybenzotriazole-1-yl) 1,1,3,3,-tetramethyluronium tetrafluoroborate; TDW refers to triple distilled water; TFA refers to trifluoroacetic acid; TOF-MS refers to time of flight mass spectrometry; Z refers to benzyloxycarbonyl;

Natural coded amino acids are represented by three-letter codes or by single-letter code, according to IUPAC conventions.

EXAMPLES

Materials

Transport buffer: 20 mM Hepes pH 7.3, 110 mM potassium acetate, 5 mM sodium acetate, 0.5 mM EGTA, 2 mM DTT, 1 mg(/ml leupeptin, 1 mg/ml pepstatin, 1 mg/ml aprotinin, 0.1 mM PMSF.

Cultured Cells:

(a) Colo-205 (human colon adenocarcinoma cells [ATCC CCL 222]) and Hut 78 cells (human T-cell line) were maintained in RPMI 1640 medium, supplemented with 10% FCS, 0.3 gr/lit L-glutamine. 100 U/ml penicillin and 100 U/ml streptomycin (Beit Haemek, Israel). Colo-205 cells were crown to give a density of $1.2 \times 10^8$ cells/ml. Following centrifugation (600 rpm 5 min.) cells were suspended in a transport buffer whic lacks the ATP-regeneratinng system.

(b) Monolayer culture of HeLa cells was grown in DMEM growth medium supplemented with 10% FCS as previously described (Broder, et al. (1997) *FEBS Lett*. 412, 535–539). Viruses: HIV-$1_{IIIB}$ strain was kindly provided by Dr. M. Weinberg (Lady Davis Institute, Montreal Canada).

EXAMPLE 1

Synthesis of Backbone Cyclic Peptides

Backbone cyclic peptides were prepared as described before (Byk, et al. (1996) *J. Med. Chem*. 39, 3174; Bitan, et al. (1997) *J. Pept. Res*. 49, 421). Briefly, peptides were synthesized on MBHA resin (loading 0.56 meq/gr). Peptide libraries were synthesized by the SMPS "tea bags" methodology (Houghten, R. (1985) *Proc.Natl.Acad.Sci.USA* 82, 5131–5135), with 200 mg resin portions in each bag in the first library, and 300 mg resin portions in the second library. The resin was sealed in 4×5 cm polypropylene fabric bags which were placed in polypropylene boxes and shaken with a Labotron shaker (INFORS HT, Bottmingen, Germany). The synthesis of peptide 22 was performed in manual SPPS vessel. The vessel was shaken with a MilliGen 504 shaker. All amino acids were Fmoc-protected on the $N^\alpha$, except for Gly and Val which were Boc-protected. The side-chain protecting groups were: Lys(Z), Ser(Bzl), Cys(pMeOBzl). PyBroP (3eq.) was used as a coupling agent, with three-fold excess of protected amino acid, and seven-fold excess of DIEA in each coupling. All protected amino acids were pre-activated for ten minutes prior to coupling. The coupling reactions were performed for 2 hrs. The coupling of the first amino acid in each peptide was repeated twice. Capping was performed with 0.5M acetic anhydride, 0.125M of DIEA and 0.015M of HOBT in DMF for 1 hr. Fmoc deprotection was performed with 20% piperidine in DMF for 30 min. and was repeated twice each time. Fmoc-$N^\alpha$-[ω-(Boc-amino) alkiy]Gly building units for the synthesis of the library were prepared as described previously. (The teachings of WO 95/33765 and WO 97/09344 are incorporated herein in their entirety by way of reference).

The coupling, of Lys after the building unit was repeated three times. Boc deprotection was performed with 55% TFA in DCM for 2 min. and then for an additional 30 min. Lactam cyclization was performed three times using TBTU (3 eq) with 4 eq. of DIEA, after Boc deprotection. HF cleavage was performed in the Kel F system (Peptide Institute, Osaka, Japan). Thioanisole was used as a scavenger in the first library, and anisole was used for the same purpose in the cleavage of the other peptides. The reaction took place at –5° C. for 2 hrs. After HF evaporation the cleaved peptides and the resin were treated with TFA, the resin was filtered off and washed 3 times with 2 ml TFA. The combined TFA washing were evaporated under nitrogen,en and the crude peptide was precipitated from cold ethyl ether. The crude peptide was washed several times with cold ether, dried, dissolved in 30% acetic acid and lyophilized. The crude peptides were analyzed by TOF-MS and had the expected molecular weights. The first library was analyzed as mixtures . All other peptides were characterized separately. The peptides were analyzed by HPLC (Merck Hitachi 655A equipped with a L-6200A gradient pump and a UV-vis detector with tunable wavelength set to 215 nm). The flow was fixed at I ml/min and the gradient was 5–60% Acetonitrile:TDW (containing 0.1% and 0.085% TFA respectively) in 3 5 min. The column was RP-3 from Shandon. Peptides 17–20 ,19.1–19.4, 21 and 22 were also characterized by AAA. Peptides 19.1–19.4, 21 and 22 were purified by Semi-preparative HPLC. The separations were performed on Lichosorb RP-8 250×10 mm i.d. column (Merck) with a constant flow of 4.5 ml/min. The gradient was 5–60% Acetonitrile.TDW (containing 0.1% and 0.085% TFA respectively) in 45 min. The purified peptides were also characterized by analytical HPLC, AAA and TOF-MS.

EXAMPLE 2

Synthesis of Lineal Peptides

Linear NLS peptides were synthesized on Rink amide resin (loading 0.5 mmol/gr) using the Applied Biosystems Peptide Synthesizer model 433A, by the FastMoc™ chemistry. The peptides were cleaved from the resin using TFA with 5% anisole as a scavenger, precipitated from cold ether, dissolved in 30% acetic acid and lyophilized. Crude peptides were analyzed by reverse-phase HPLC (C3 column, gradient of 5–60% acetonitrile:TDW containing 0.1% TFA, 35 min.) and characterized by TOF-MS and amino acid analysis.

EXAMPLE 3

Quantitative Analysis of Nuclear Import in an In-vitro System.

Nuclear import was quantitatively determined essentially as described before (Melchior, et al. (1993) *J. Cell. Biol*. 123 (6). 1649–1659), except that a suspension of Colo-205 cells was used instead of a suspension of HeLa cells and 500 nM biotinylated BSA-NLS were used as a transport substrate. The immunomodule strips were coated with rabbit anti-BSA serum instead of using the IgG fraction. The results given are an average of triplicate determination whose standard deviation never exceeded ±20%.

EXAMPLE 4

Estimation of Nuclear Import by Fluorescence Microscopy Observations.

HeLa cells were cultivated on 10 mm coverslips to subconfluent density and then permeabilized with digitonin as described before (Broder, et al. ibid). Linear peptides bearing the NLS signal of the SV40 large T-antigen were covalently attached to fluorescently labeled (with FITC) BSA molecules (Goldfarb, et al. (1986) *Nature* 322, 641–644) and translocation of the resulting fluorescently labeled-NLS-BSA molecules (FL-NLS-BSA) into nuclei of digitonin-permeabilized HeLa cells was followed by fluorescent microscopy observations, as described (Broder, et al. ibid).

EXAMPLE 5

Design, Synthesis and Screening of the First Backbone Cyclic NLS-mimetic Library The design of the backbone cyclic peptide library was based on the structure of HIV-1 MA as determined by NMP (Massiah, et al. (1994) *J.Mol.Biol.* 244, 198–223; Matthews, et al. (1994) *Nature* 370, 666–668). The sequence of the NLS region in this protein is -KKQYK- or -KKKYK- in other HIV-1 strains (Massiah, et al. (1994) *J.Mol.Biol.* 244, 198–223), and it is located within the outer strand of a β-sheet. Residues K26,K27,Q28 and K30 are exposed to the solvent, while the side chain of Y29 faces the interior of the protein, forming a hydrogen bond with T97. Replacement of Tyr29 by a Phe residue significantly reduced nuclear uptake of the HIV-1 MA (Von-Schwedler, et al. ibid). Since Y29 is not exposed to the surface of the protein we have assumed that its role is to stabilize the bioactive conformation of the NLS region. Conceivably, this conformation renders the basic residues accessible for bindings to the putative NLS-receptor (Gorlich, et al. (1994) (*Cell* 79,767–778). This assumption led us to design the first peptide library in such a way that the backbone cyclic building unit would replace Y29. The role of the building unit is to mimic that of Y29, namely to impose a conformational constraint (by cyclization) on the NLS. A ring size cycloscan was also performed in the first library to determine the optimal ring size required for inhibitory effect.

Figure 1:
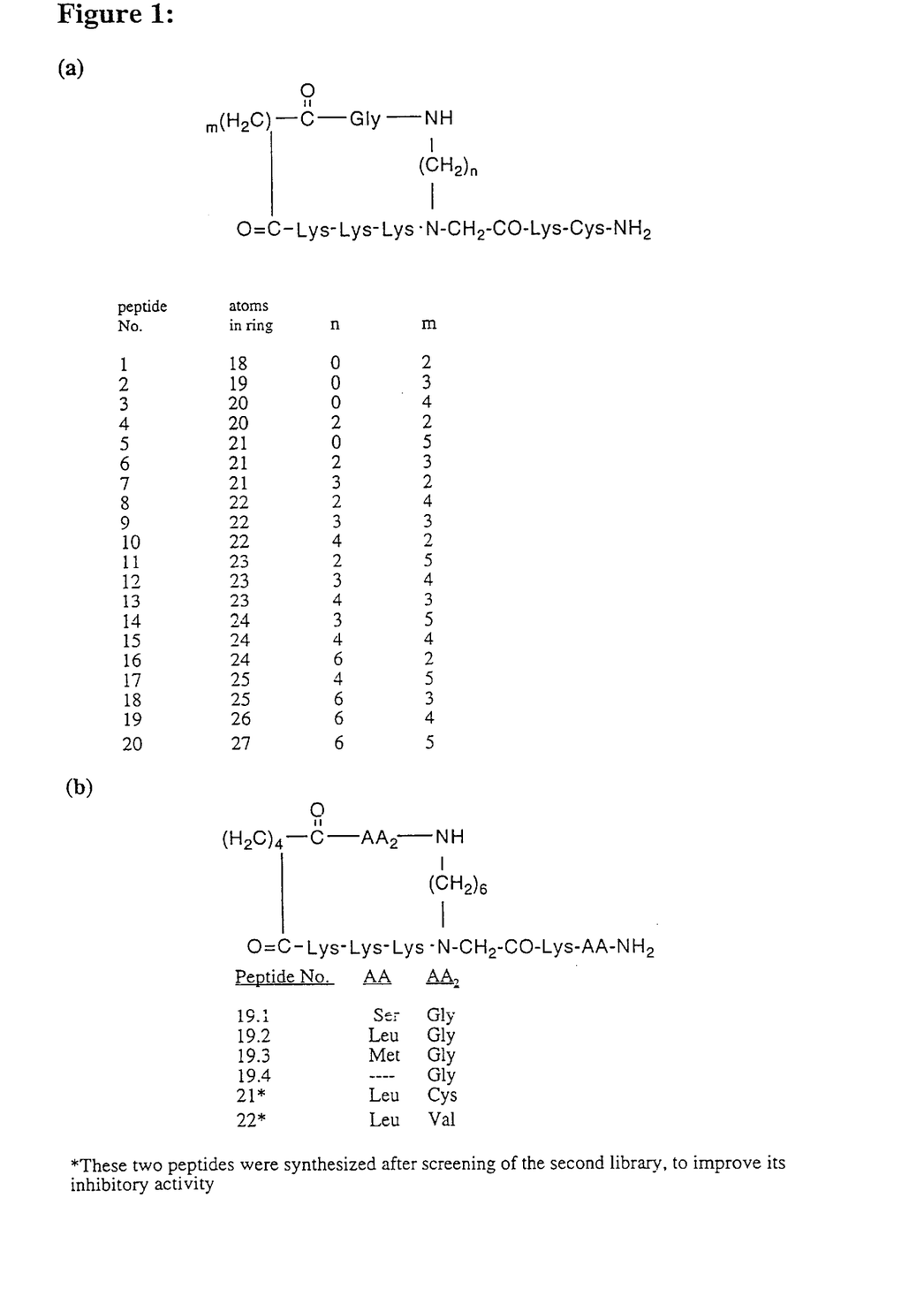
FIGS. 1(a)–1(b): General structure of the backbone cyclic NLS-mimetic peptides: (a) first library, (b) second library.

Based on the information described above we designed an N-backbone to end cyclic library of 20 peptides with the general structure shown in FIG. 1a. The backbone cyclic building unit used had a free amine at the end of the N-alkyl chain, and the lactam ring cyclization was formed by an amide bond to a dicarboxylic acid spacer attached to the N-terminus of the peptide.

Initial screening of the first library was performed by estimating the ability of its peptides to competitively inhibit nuclear translocation of FL-NLS-BSA in the in vitro system (example 3). The library was divided into four crude peptide mixtures which were screened separately. Out of these mixtures only one, designated mixture 4 (containing peptides 17–20, see FIG. 1a) was found to possess an inhibitory activity. The activity of each individual crude peptide present in mixture 4 was then determined by the same method, from which peptide 19 (ring size of 26 atoms) was found to be the most potent inhibitor and served as a lead compound for a second library.

EXAMPLE 6

Design, Synthesis and Screening of the Second Backbone Cyclic NLS-mimetic Library To optimize the inhibitory activity of the NLS-mimetic lead compound (peptide 19), we designed and synthesized a second library having the general structure shown in FIG. 1b. In this library, the ring size and ring position were maintained as in peptide 19, and an amino acid scan was performed both in the ring and in the parent sequence. The cysteine residue, which is not an integral part of the NLS sequence, was replaced by various amino acids. The activity of the crude peptides (designated 19.1–19.4) was determined by fluorescent microscopy (example 4). Out of which two peptides, 19.2 and 19.4, were found to be inhibitory. The $IC_{50}$ values of the purified peptides from this library in comparison to that of the corresponding linear parent NLS peptides are shown in Table 2. Peptide 19.2 was found to be the most active backbone cyclic peptide, with an $IC_{50}$ value of 3 μM. To improve the inhibitory activity, this peptide was used as a lead compound for further iterations of the cycloscan procedure.

TABLE 2

| Peptide structure | Peptide name | $IC_{50}$ (μM) |
|---|---|---|
| Pro—Lys—Lys—Lys—Arg—Lys—Val—Cys—NH₂ (SEQ ID NO: 1) | SV40 large T-antigen NLS | 0.001 |
| [cyclic structure: (H₂C)₄—C(=O)—Val—NH—(CH₂)₆; O=C—Lys—Lys—Lys—N—CH₂—CO—Lys—Leu—NH₂] | 22 (BCvir) | 0.04 |
| [cyclic structure: (H₂C)₄—C(=O)—Gly—NH—(CH₂)₆; O=C—Lys—Lys—Lys—N—CH₂—CO—Lys—Leu—NH₂] | 19.2 | 3 |
| Gly—Lys—Lys—Lys—Tyr—Lys—Leu—Lys—His—Cys—NH₂ (SEQ ID NO: 2) | HIV-MA NLS | 12 |
| [cyclic structure: (H₂C)₄—C(=O)—Gly—NH—(CH₂)₆; O=C—Lys—Lys—Lys—N—CH₂—CO—Lys—NH₂] | 19.4 | 150 |

TABLE 2-continued

| Peptide structure | Peptide name | $IC_{50}$ ($\mu M$) |
|---|---|---|
| (H₂C)₄—C(=O)—Gly—N(H)—(CH₂)₆<br>\|                                                  \|<br>O=C—Lys—Lys—Lys—N—CH₂—CO—Lys—Ser—NH₂ | 19.1 | >1000 |
| (H₂C)₄—C(=O)—Cys—N(H)—(CH₂)₆<br>\|                                                  \|<br>O=C—Lys—Lys—Lys—N—CH₂—CO—Lys—Leu—NH₂ | 21 | no inhibition |

Figure 2:
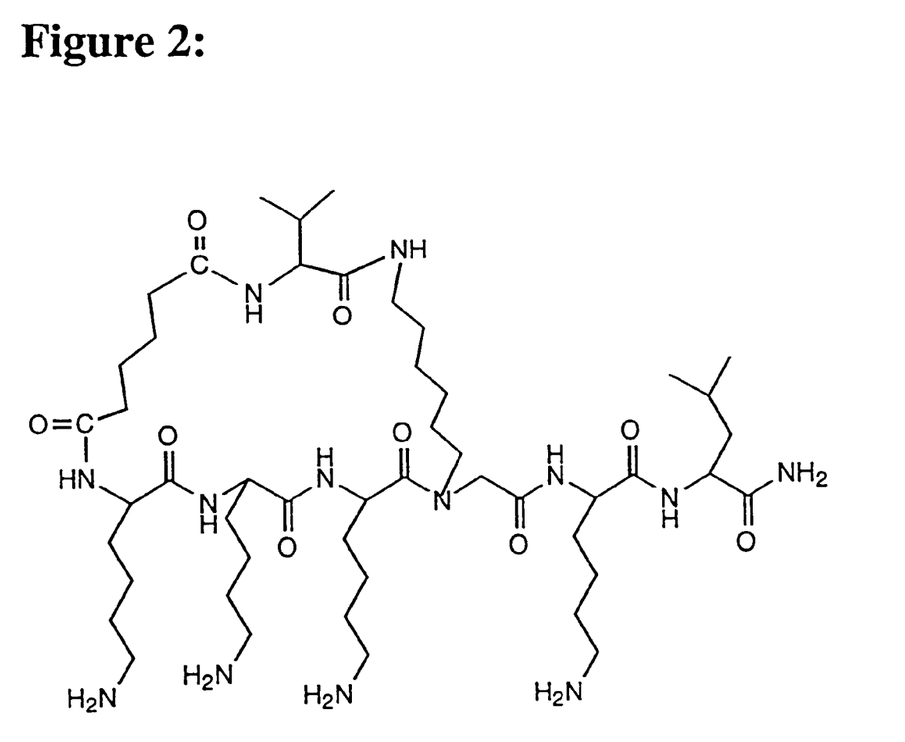
FIG. 2 Structure of Bcvir

This results show that the lead peptide 19.2 is much less potent than the prototypic SV40 NLS, but is already more potent than the HIV-MA NLS. We assumed that the relatively low activity of peptide 19.2 is due to the fact that the Gly residue in the ring is indifferent to the expected β-structure, resulting in a peptide with a less stable β-structure. In order to further stabilize the β-structure and thereby improve the inhibitory activity of peptide 19.2, the Gly residue was replaced by a Val residue which is known to be the best β-sheet former (Smith, et al. (1994) *Biochemistry* 33, 5510–5517). The structure of the resulting new peptide, which was designated by us BCvir (peptide 22), is shown in FIG. 2. As anticipated, the purified BCvir was found to be highly active and its $IC_{50}$ value reached 35 nM, two orders of magnitude better than that of the lead compound, 19.2. For comparison, the $IC_{50}$ value of the linear parent peptide, namely that of the HIV-1 MA NLS was 12 $\mu M$.

Figure 3:
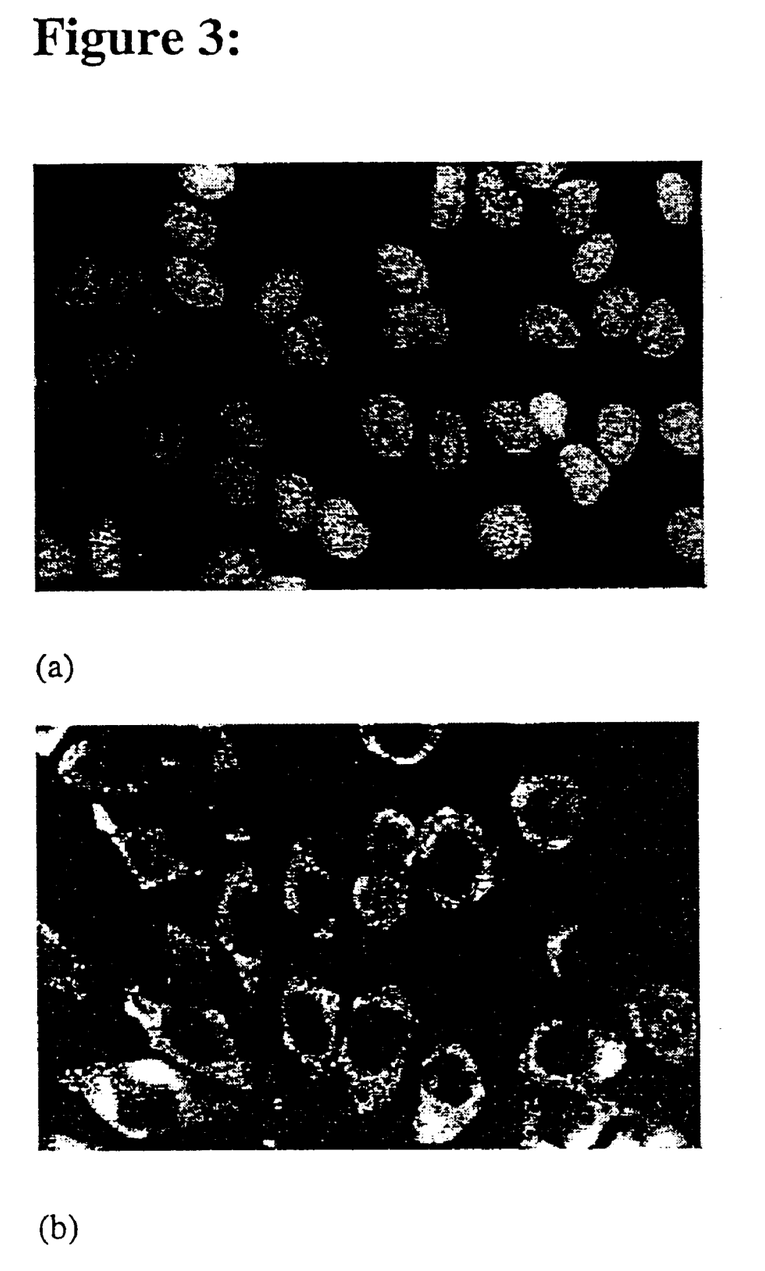
FIGS 3(a)–3(b): BCvir inhibits the Translocation of FL-NLS-BSA into nuclei of permeabilized HeLa cells. Permeabilized HeLa cells were incubated with FL-NLS_BSA, in the absence (a) or in the presence (b) of BCvir. The inhibitory BCvir was added in a ration of BCvir: transport substrate of 2:1 (w/w).

The above results were confirmed by nuclear import of fluorescently labeled NLS-BSA and fluorescent microscopy observations (example 4). As can be seen in FIG. 3, BCvir completely abolished nuclear import.

EXAMPLE 7

Stability of BCvir to Proteolytic Cleavage by Trypsin

Method: A mixture containing 0.05 ml of trypsin solution (8% w/v in HCl 0.001M), 0.5 ml TEA buffer pH=7.8 (Geiger, R.; Fritz, H. *In Methods of enzymatic analysis*; H. U. Bergmeyer, et al. Eds.; Weinheim: Verlag-chemie: 1984; pp 119–129) and 0.2 ml of peptide 22 (BCvir) solution in water (initial concentration of 1.25 mg/ml) was injected to HPLC (C3 column, gradient of 5–60% acetonitrile:TDW containing 0.1% TFA, 35 minutes) immediately after addition of the peptide (t=0). The mixture was incubated at room temperature and samples were injected every 70 min. The same experiment was performed with peptide 19.4 (initial concentration 3 mg/ml) and with the HIV-MA NLS linear peptide (initial concentration 20 mg/ml). The peak area of the peptide at each time interval was compared to the peak area of the peptide in t=0, as a measure of the relative peptide concentration.

Figure 4:
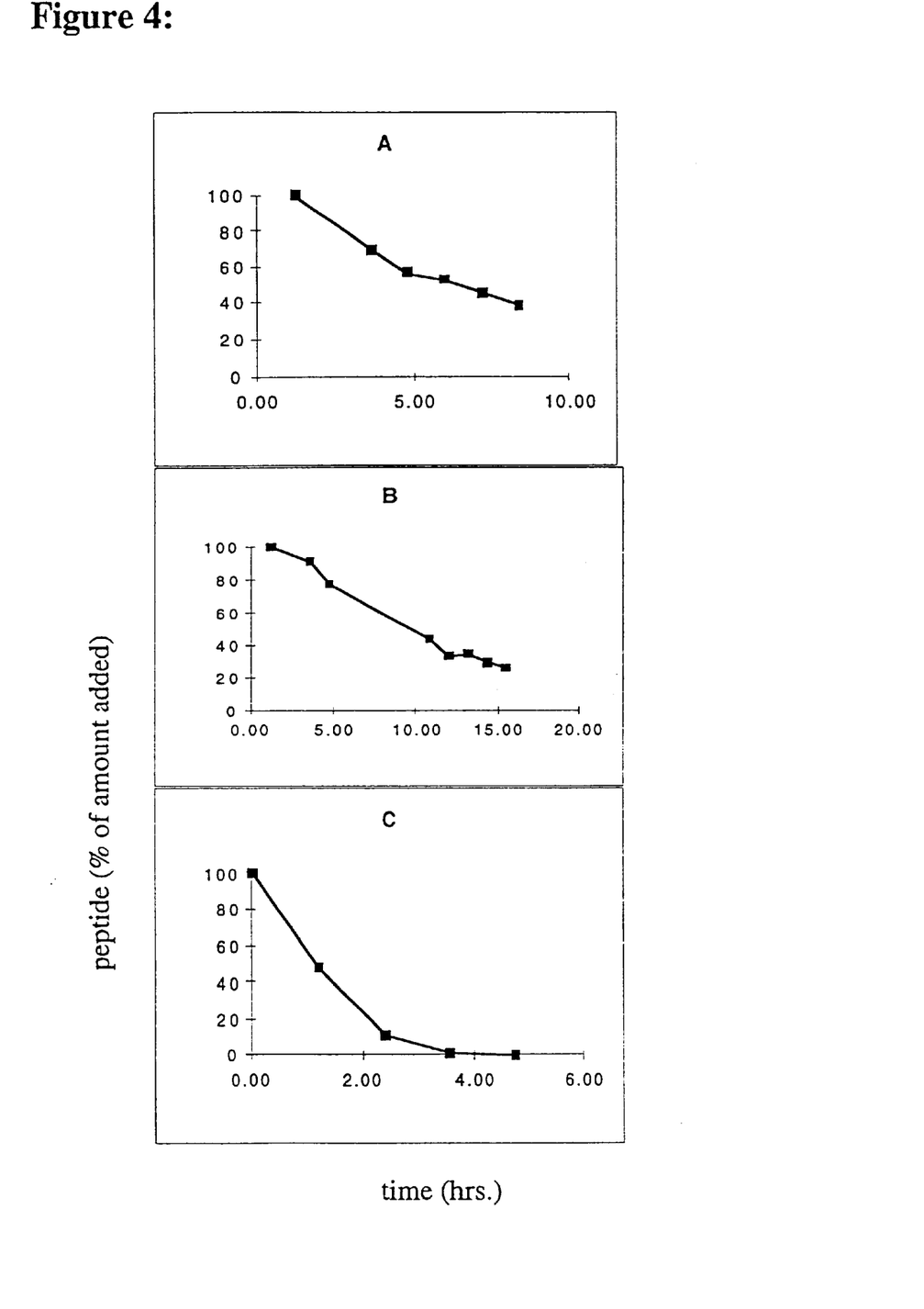
FIGS. 4(A)–4(C): Determination of the susceptibility of BCvir, peptide 19.4 and HIV-MA NLS to tryptic digestion. (A) BCvir (B) peptide 19.4 (C) HIV-MA NLS linear peptide. The half life (t½) values are 7, 9, and 1.3 hours repectively.

Results: BCvir contains four lysine residues, and therefore it was important to study its susceptibility to proteolytic cleavage by trypsin. As mentioned above, backbone cyclic peptides are expected to be relatively resistant to proteolytic digestion. The results given in FIG. 4 show that the t½ value of BCvir digestion by trypsin is 7 hours, that of peptide 19.4 9 hours and that of the linear HIV-MA NLS parent peptide is only about 1.3 hours. Evidently, BCvir possesses a relatively high resistance to cleavage by trypsin as reflected by its long t½ value. Based on the HPLC chromatogram, in which the area of the peak corresponding to BCvir decreased and the area of another peak with a shorter retention time increased, we assume that the exocyclic lysine-leucine bond in BCvir was slowly cleaved. Proteolysis within the ring would result in multiple product peaks. This assumption is supported by the results showing that peptide 19.4, which lacks an exocyclic peptide bond, has a longer t½ value.

EXAMPLE 8

Inhibition of HIV-1 Production by BCvir.

Method: Hut 78 cells (0.5×10⁶/ml) were incubated for 2 hrs at 37° C. with or without 5 $\mu g/ml$ aphidicholine. Cells were then infected with HIV-1$_{IIIB}$ (at a multiplicity of infection of 0.1) in the presence or absence BCvir (100 $\mu g/ml$). Following 1 hr absorption, cells were incubated in 1.5 ml of the same media and samples of 120 $\mu l$ were taken on 3, 5 and 7 and 9 days post infection. Virus propagation was determined according to the amounts of p24-CA antigen released into the media, using a Vironostika HIV-1 Antigen MicroELISA system (Organon Teknika, USA).

Figure 5:
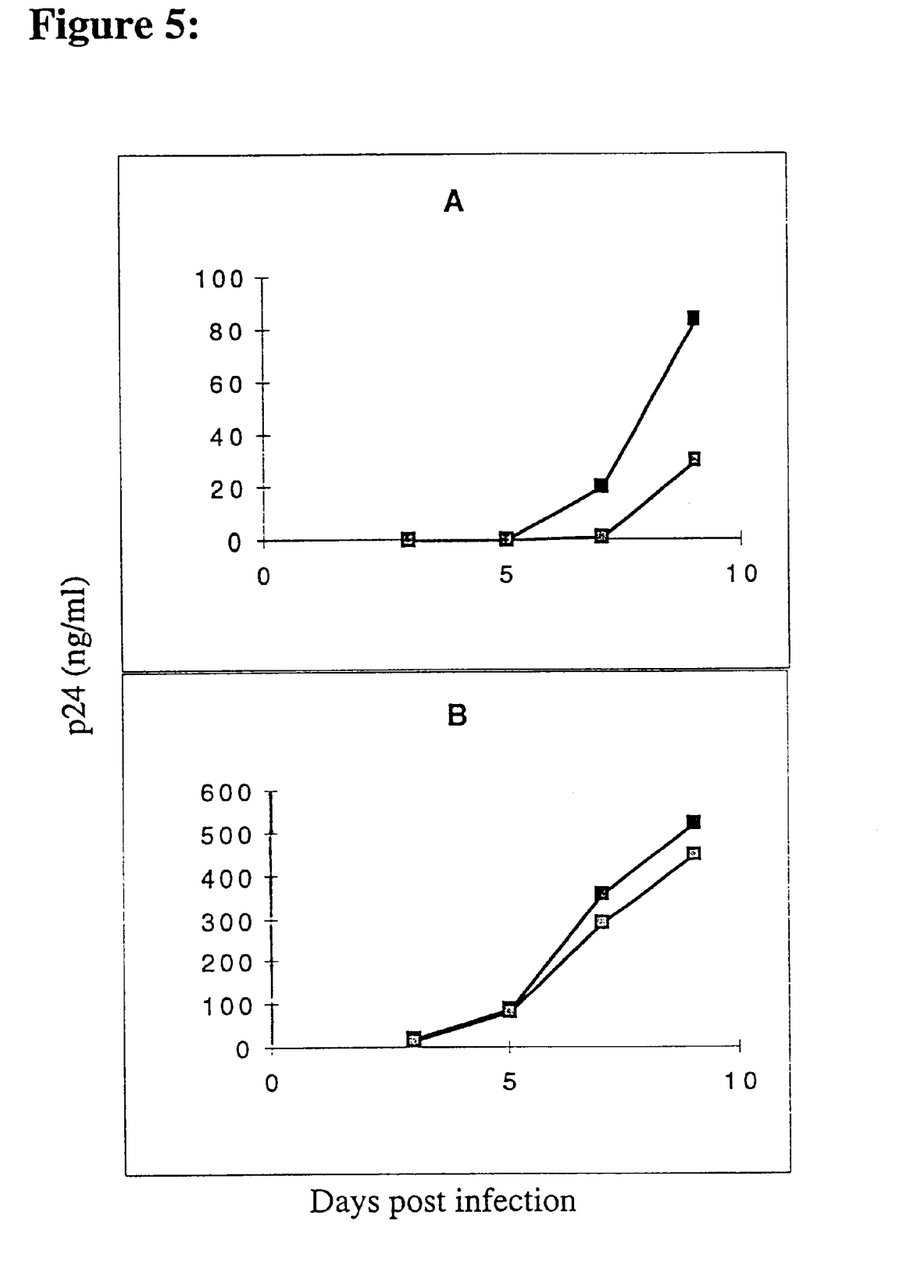
FIGS. 5(A)–5(B): Inhibition of HIV-1 production by BCvir: BCvir was added to human Hut 78 cells infected by HIV-1 two hours prior to infection. (A) Inhibition of HIV-1 growth by BCvir in cell-cycle arrested human Hut 78 cells {without BCvir; with BCvir}. (B) No inhibition by the same peptide in dividing cells {without BCvir; with BCvir}.

Results: Since BCvir inhibited nuclear import of NLS-BSA in a cell-free system, we tested its effect on HIV-1 production in virus infected cells. Since the MA NLS is essential for HIV-1 replication only in non-dividing cells (Von-Schwedler, et al. ibid; Bukrinsky, et al. ibid), the effect of BCvir was studied in aphidicholine cell-cycle arrested cells. FIG. 5A shows that 9 days post infection BCvir (100 $\mu g/ml$) reduced virus production by 75% in non-dividing Hut 78 cells, when compared to virus production in untreated cells. BCvir did not affect virus production in aphidicholine-untreated dividing cells (FIG. 5B). Please note that virus production in cells grown in the absence of aphidicholine is more efficient than in cells grown in its presence.

EXAMPLE 9

Determination of BCvir Cytotoxicity

Method: Hut 78 cells (0.5×10⁶/ml) were cultured without or with 0.1, 1, 10 and 100 $\mu g/ml$ of BCvir. The number of living cells was determined by staining with trypan blue 1, 2, 4 and 7 days post seeding,.

Results: BCvir did not affect the growth rate of uninfected cultured Hut 78 cells.

EXAMPLE 10

Inhibition of SV40-NLS-BSA Nuclear Uptake by Peptides Derived from the HIV-1 Vif Protein and Other NLS Peptides Derived from HIV-1 Proteins Nuclear uptake was determined by the ELISA-based assay, except where indicated. $IC_{50}$ values were determined by using peptides and transport substrates in molar ratios between 500:1 and 0.005:1 respectively. Cysteine residues in all the peptides are not part of the original sequence and were added in order to conjugate them to BSA. The results are described in table 3 below.

TABLE 3

| Peptide | Sequence (1) | Nuclear uptake of SV40-BSA | $IC_{50}$ ($\mu$M) |
|---|---|---|---|
| Vif 30-44 (3) | $^{30}$YVSGKARGWFYRHHY$^{44}$ (SEQ ID NO: 3) | + | – |
| Vif 41-55 (3) | $^{41}$RHHYESPHPRISSEV$^{55}$ (SEQ ID NO: 4) | + | – |
| Vif 51-65 (3) | $^{51}$ISSEVHIPLGDARLV$^{65}$ (SEQ ID NO: 5) | + | – |
| Vif 78-85 (3) | $^{78}$DWHLGQGV$^{85}$ (SEQ ID NO: 6) | + | – |
| Vif 78-92 | $^{78}$DWHLGQGVSIEWRKK$^{92}$ (SEQ ID NO: 7) | N.D. | |
| Vif 85-92 | $^{85}$VSIEWRKK$^{92}$ (SEQ ID NO: 8) | – | 253 |
| Vif 88-98 | C$^{88}$EWRKKRYSTOV$^{98}$ (SEQ ID NO: 9) | – | 62 |
| Vif 88-98 K91L | C$^{88}$EWRKKRYSTOV$^{98}$ (SEQ ID NO: 10) | + | – |
| Vif 88-95 | $^{88}$EWRKKRYS$^{95}$ (SEQ ID NO: 11) | – | N.D. |
| SV40-NLS | PKKKRKVC (SEQ ID NO: 12) | – | 0.02 |
| SV40 mutant (2) | CGPKNKRKV (SEQ ID NO: 13) | + | – |
| SV40 reverse | CVKRKKKPG (SEQ ID NO: 14) | + | – |
| HIV-MA NLS | C$^{25}$GKKKYKLKH$^{33}$ (SEQ ID NO: 15) | – | 36 |
| Tat NLS | C$^{48}$GRKKRRQRRRAHQN$^{61}$ (SEQ ID NO: 16) | – | 147 |
| Rev NLS | C$^{35}$RQARRNRRRRWRERQRQ$^{51}$ (SEQ ID NO: 17) | – | 347 |
| Nef NLS | C$^{7}$KRSMGGWSAIRERMRR$^{22}$ (SEQ ID NO: 18) | – | 11 |

(1) Numbers indicate the position of the residues within the intact protein. Residues included in the putative NLS of Vif are bolded.
(2) Mutated residue is bolded. Note that the mutant and reverse SV40-NLS peptides did not show any inhibitory effect.
(3) These results are based on fluorescent microscopy observations.
(+) most of the cells in the field (more than 70–80%) did show nuclear uptake (presence of fluorescent dye within the nuclei).
(–) most of the cells in the field (more than 70–80%) did show nuclear uptake (their cytoplasm, and not the nuclei, were fluorescently labeled).

EXAMPLE 11

Promotion and Inhibition of Nuclear Uptake by Peptides Derived from HIV-1 Proteins The indicated peptides (for the appropriate sequences see table 3) were conjugated to labeled BSA molecules and nuclear import of the resulting conjugate was estimated by the ELISA-based assay as described above.

Inhibition of nuclear uptake was estimated by addition of the above listed peptides to a nuclear transport system using SV40-NLS-BSA as a transport substrate.

The results given in table 4, except for Vif 88–98, were confirmed by fluorescent microscopy observations (example 4).

TABLE 4

| Peptide | Promotion of nuclear import of the peptide-BSA conjugate | Inhibition of nuclear import by the free peptide |
|---|---|---|
| SV40-NLS | + | + |
| SV40 NLS mutant | – | – |
| Vif 88-98 | – | + |
| Tat-NLS | + | + |

TABLE 4-continued

| Peptide | Promotion of nuclear import of the peptide-BSA conjugate | Inhibition of nuclear import by the free peptide |
|---|---|---|
| BCvir | – | + |
| MA-NLS | – | + |

EXAMPLE 12

Determination of the Number of NLS Peptides Conjugated to BSA Molecule in the Different Conjugates The average number of NLS peptides conjugated to each BSA molecule was determined by amino acid analysisResults are summarized in table 5. .

TABLE 5

| Conjugate | Average number of NLS peptides/BSA molecule |
| --- | --- |
| SV40-NLS-rho-BSA | 6.7 |
| Tat-NLS-rho-BSA | 3 |
| SV40-NLS-biotin-BSA | 4 |
| Tat-NLS-biotin-BSA | 3 |
| Vif 88-98-biotin-BSA | 4.5 |

EXAMPLE 13

Characterization of the Nuclear Import of Tat-NLS-BSA

Peptides bearing the sequences of Tat-NLS and the NLS of SV40 large T-antigen were synthesized and conjugated to biotinylated BSA.

The entry of the conjugates into nuclei of permeabilized colo cells was estimated as described above. ATP was depleted, WGA (0.6 mg/ml) and Tat-NLS peptide (1 mg/ml) were preincubated for 30 minutes at room temperature with the permeabilized cells before adding the BSA conjugates. Results are shown in table 6.

TABLE 6

|  | Tat-NLS-BSA | SV40-NLS-BSA |
|  | Nuclear entry (%)* | |
| --- | --- | --- |
| With cytosolic factors | 100 | 100 |
| Without cytosolic factors | 100 | 14.9 |
| without ATP | 15.1 | 13.3 |
| WGA | 53.6 | 49.8 |
| Tat-NLS peptide | 15.4 | 52 |

*entry of each conjugate in the presence of cytosolic factors was considered as 100%.

EXAMPLE 14

Screening of the Backbone Cyclic Tat-NLS Mimetic Library

Nuclear transport using SV40-NLS-BSA and Tat-NLS-BSA as transport substrates was performed employing the in-vitro ELISA system. The results are shown in table 7.

TABLE 7

| Transport substrate Backbone cyclic Peptide (1 mg/ml) | SV40-NLS-BSA* | Tat-NLS-BSA | Tat-NLS without cytosolic factors |
| --- | --- | --- | --- |
| | (% inhibition on the corresponding transport substrate) | | |
| Tat-4 | −206 | 102.2 | 101.3 |
| Tat-5 | −16 | 58.7 | 74.5 |
| Tat-6 | −47 | 45.7 | 66.4 |
| Tat-7 | −390 | 9.8 | 44.3 |
| Tat-8 | −97 | −18.5 | 26.8 |
| Tat-9 | −191 | 106.5 | 104 |
| Tat-10 | −52 | 106.5 | 104 |
| Tat-11 | −161 | 48.9 | 68.5 |
| Tat-12 | −119 | 48.9 | 68.5 |
| Tat-13 | −5 | 66.3 | 79.2 |
| Tat-14 | −38 | 48.9 | 68.5 |
| Tat-15 | −13 | −29.3 | 20.1 |
| Tat-16 | −20 | 79.3 | 87.2 |

*A negative value for % inhibition indicates activation of nuclear transport.
**Nuclear transport of Tat-NLS-BSA in the in-vitro assay system does not require the addition of soluble cytosolic factors, since Tat-NLS promotes nuclear uptake in a non-importin pathway.

EXAMPLE 15

Vpr NLS Mimetics

Viral protein r (Vpr), an HIV-1 auxiliary protein which mediates nuclear import of the viral preintegration complex (PIC), contains two regions, N- and C-terminal, which have been proposed to function as a nuclear localization signal (NLS). We have synthesized peptides corresponding to both regions (designated as VprN and VprC), conjugated them to bovine serum albumin (BSA), and tested their ability to mediate nuclear import in permeabilized cells. Only VprN, and not VprC, functioned as an active NLS and promoted translocation of the conjugate into nuclei. Nuclear import of the conjugate was found to be energy and temperature dependent and was inhibited by wheat germ agglutinin (WGA). However, it did not require the addition of cytosolic factors and was not inhibited by the prototypic SV40 large T-antigen NLS peptide. Our results show that Vpr harbors a non-conventional negatively charged NLS and therefore suggest that Vpr may use a distinct nuclear import pathway.

General Conclusions

The present disclosure demonstrates a successful application of the novel approach of BC proteinomimetics to obtain a functional mimetic of an active region that bears a defined secondary structure within a viral protein. This was demonstrated by the discovery of backbone cyclic peptides, whose amino acid sequences correspond to the NLS of the HIV proteins, which were able to inhibit nuclear import in an in vitro assay systems as well as HIV-1 replication in infected cultured cells.

Conformational restriction renders the backbone cyclic NLS peptides less flexible and probably more selective than the linear peptides. In addition, the backbone cyclic peptides are resistant to proteolysis, a fact that should potentate their metabolic stability. Being metabolically stable makes such backbone cyclic peptides attractive candidates for therapeutic applications.

Evidently, such an approach may be essential in cases when the NLS region is composed of discontiguous amino acid residues, e.g. bipartite NLS sequences.

Blocking of HIV nuclear import as a therapeutic objective was already suggested and the use of small non-peptidic molecules for that purpose was demonstrated (Dubrovsky, et al. (1995) Mol. Med. 1 (2), 21 7–230). Due to their inherent properties and their ability to block nuclear import, backbone cyclic peptides from the type disclosed herein constitute candidates for the development of a novel class of anti-viral drugs in general, and anti-HIV drugs in particular.

Irrespective of the mechanism involved the novel backbone cyclized peptides which mimic NLS sequences of macromolecules are claimed as such, as pharmaceutical compositions comprising as an active ingredient a therapeutically effective amount of a backbone cyclic peptide which mimics the NLS sequence of a macromolecule and for their utility in inhibiting the transfer of macromolecules from the cytoplasm to the nucleus.

The methods of the present invention are exemplified herein using backbone cyclic peptides which mimic the NLS sequence of HIV-1 proteins MA, Tat and Vpr or mimic the sequence spanning residues 88–98 of Vif, which comprises an NLS like sequence having basic residues. The peptides disclosed are shown to inhibit the replication of virus in infected cells.

The skilled artisan will appreciate that the above examples are merely illustrative and serve as non limitative exemplification of the present invention and that many variations and modifications are possible within the scope of the currently claimed invention as defined by the claims which follow.

What is claimed is:

1. A backbone cyclic peptide which inhibits transfer of macromolecules from the cell cytoplasm to the cell nucleus, wherein the macromolecules enter the nucleus by the mediation of a nuclear localization signal and said backbone cyclic peptide comprises a peptide sequence having an $N^\alpha$-derivative of an amino acid, wherein at least one $N^\alpha$ backbone nitrogen in the peptide sequence is linked to a side chain of at least one other amino acid in the peptide sequence or to at least one other backbone nitrogen in said peptide sequence.

2. The backbone cyclic peptide of claim 1 wherein the peptide is a nuclear localization signal sequence of a macromolecule, which macromolecule enters the nucleus by the mediation of said nuclear localization signal sequence.

3. The backbone cyclic peptide of claim 1 wherein the peptide is a nuclear localization signal sequence of a viral protein.

4. The backbone cyclic peptide of claim 3 wherein the peptide is a nuclear localization signal sequence of an HIV-1 protein.

5. The backbone cyclic peptide of claim 4 wherein the peptide is a nuclear localization signal sequence selected from the HIV-1 proteins matrix protein, tyrosine aminotransferase (Tat), and viral protein r (Vpr) or residues 88–98 of the HIV-1 protein virion infectivity factor (Vif).

6. A backbone cyclic peptide for inhibiting transfer of macromolecules from the cell cytoplasm to the cell nucleus, wherein the macromolecules enter the nucleus by the mediation of a nuclear localization signal and the peptide is of the formula I:

Formula I wherein n denotes an integer from 1 to 10 or may be zero, with the proviso that when n is zero NH is also absent; m denotes an integer from 1 to 10; R denotes lysine or glutamine; AA and $AA_2$ independently denote an amino acid residue which may be the same or different.

7. The backbone cyclic peptide of claim 6 having the formula II:

Formula II wherein n denotes an integer from 1 to 10 or may be zero, with the proviso that when n is zero NH is also absent; m is an integer from 1 to 10; R denotes Lys or Gln.

8. The backbone cyclic peptide of claim 6 having the formula III:

Formula III wherein R denotes Lys or Gln, AA denotes an amino acid residue selected from the group consisting of serine, leucine or methionine, and $AA_2$ denotes an amino acid residue selected from the group consisting of valine, glycine or cysteine.

9. The backbone cyclic peptide of claim 8 wherein R is Lysine, AA is Leucine and $AA_2$ is Valine.

10. The backbone cyclic peptide of claim 1 having the formula IV:

Formula IV wherein m and n are each independently an integer from 1 to 10.

11. A composition comprising a suitable carrier, and a backbone cyclic peptide according to claim 1, in an amount sufficient to inhibit transfer of macromolecules from the cell cytoplasm to the cell nucleus.

12. The composition of claim 11 wherein the peptide is a nuclear localization signal sequence of a macromolecule which enters the nucleus by the mediation of said nuclear localization signal sequence.

13. The composition of claim 11 wherein the peptide is a nuclear localization signal sequence of a virus.

14. The composition of claim 13 wherein the peptide is of the nuclear localization signal sequence of Human Immunodeficiency Virus (HIV-1).

15. The composition of claim 14 wherein the peptide is a nuclear localization signal sequence selected from the HIV-1 proteins matrix protein, tyrosine aminotransferase (Tat), and viral protein r (Vpr) or residues 88–98 of the HIV-1 protein virion infectivity factor (Vif).

16. A composition comprising a suitable carrier, and a backbone cyclic peptide in an amount sufficient to inhibit transfer of macromolecules from the cell cytoplasm to the cell nucleus, wherein the backbone cyclic peptide is of the formula I:

Formula I wherein n denotes an integer from 1 to 10 or may be zero, with the proviso that when n is zero NH is also absent; m denotes an integer from 1 to 10; R denotes lysine or glutamine; AA and $AA_2$ independently denote an amino acid residue which may be the same or different.

17. The composition of claim 16 wherein the backbone cyclic peptide is of the formula II:

Formula II wherein n denotes an integer from 1 to 10 or may be zero, with the proviso that when n is zero NH is also absent; m is an integer from 1 to 10; R denotes Lys or Gln.

18. The composition of claim 16 wherein the backbone cyclic peptide is of the formula III:

Formula III wherein R denotes Lys or Gln, AA denotes an amino acid residue selected from the group consisting of serine, leucine or methionine, and $AA_2$ denotes an amino acid residue selected from the group consisting of valine, glycine or cysteine.

19. The composition of claim 18 wherein R is Lysine, AA is Leucine and $AA_2$ is Valine.

20. The composition of claim 14 wherein the backbone cyclic peptide is of formula IV:

Formula IV wherein m and n are each independently an integer from 1 to 10.

21. A method for inhibiting transfer of macromolecules from the cell cytoplasm to the cell nucleus, wherein the macromolecules enter the nucleus by the mediation of a nuclear localization signal, said method comprising contacting the cell with an effective amount of the backbone cyclic peptide of claim 1.

22. The method of claim 21 wherein the peptide is a nuclear localization signal sequence of the macromolecule.

23. The method of claims 21 wherein the peptide is a nuclear localization signal sequence of a virus.

24. The method of claim 23 wherein the peptide is a nuclear localization signal sequence of HIV-1.

25. The method of claim 24 wherein the peptide is a nuclear localization signal sequence selected from the HIV-1 proteins matrix protein, tyrosine aminotransferase (Tat), and viral protein r (Vpr) or residues 88–98 of the HIV-1 protein virion infectivity factor (Vif).

26. A method for inhibiting transfer of macromolecules from the cell cytoplasm to the cell nucleus, wherein said macromolecules enter the nucleus by mediation of a nuclear localization signal, said method comprising contacting the cell with a cyclic peptide of formula I:

Formula I for a time and under conditions effective to inhibit transfer of said macromolecules from the cell cytoplasm to the cell nucleus, wherein n denotes an integer from 1 to 10 or may be zero, with the proviso that when n is zero NH is also absent; m denotes an integer from 1 to 10; R denotes lysine or glutamine; AA and $AA_2$ independently denote an amino acid residue which may be the same or different.

27. The method of claim 26 wherein the peptide is of the formula II:

Formula II wherein n denotes an integer from 1 to 10 or may be zero, with the proviso that when n is zero NH is also absent; m is an integer from 1 to 10; R denotes Lys or Gln.

28. The method of claim 26 wherein the peptide is of the formula III:

Formula III wherein R denotes Lys or Gln, AA denotes an amino acid residue selected from the group consisting of serine, leucine or methionine, and $AA_2$ denotes an amino acid residue selected from the group consisting of valine, glycine or cysteine.

29. The back bone cyclic peptide of claim 28 wherein R is Lysine, AA is Leucine and $AA_2$ is Valine.

30. The backbone cyclic peptide of claim 21 wherein the peptide is of the formula IV:

Formula IV wherein m and n are each independently an integer from 1 to 10.

* * * * *

SEQUENCE LISTING

```
<160> NUMBER OF SEQ ID NOS: 20

<210> SEQ ID NO 1
<211> LENGTH: 8
<212> TYPE: PRT
<213> ORGANISM: Human Immunodeficiency Virus (HIV-1)

<400> SEQUENCE: 1

Pro Lys Lys Lys Arg Lys Val Cys
 1               5

<210> SEQ ID NO 2
<211> LENGTH: 10
<212> TYPE: PRT
<213> ORGANISM: Human Immunodeficiency Virus (HIV-1)

<400> SEQUENCE: 2

Gly Lys Lys Lys Tyr Lys Leu Lys His Cys
 1               5                  10

<210> SEQ ID NO 3
<211> LENGTH: 15
<212> TYPE: PRT
<213> ORGANISM: Human Immunodeficiency Virus (HIV-1)

<400> SEQUENCE: 3

Tyr Val Ser Gly Lys Ala Arg Gly Trp Phe Tyr Arg His His Tyr
 1               5                  10                  15

<210> SEQ ID NO 4
<211> LENGTH: 15
<212> TYPE: PRT
<213> ORGANISM: Human Immunodeficiency Virus (HIV-1)

<400> SEQUENCE: 4

Arg His His Tyr Glu Ser Pro His Pro Arg Ile Ser Ser Glu Val
 1               5                  10                  15

<210> SEQ ID NO 5
<211> LENGTH: 15
<212> TYPE: PRT
<213> ORGANISM: Human Immunodeficiency Virus (HIV-1)

<400> SEQUENCE: 5

Ile Ser Ser Glu Val His Ile Pro Leu Gly Asp Ala Arg Leu Val
 1               5                  10                  15

<210> SEQ ID NO 6
<211> LENGTH: 8
<212> TYPE: PRT
<213> ORGANISM: Human Immunodeficiency Virus (HIV-1)

<400> SEQUENCE: 6
```

Asp Trp His Leu Gly Gln Gly Val
1               5

<210> SEQ ID NO 7
<211> LENGTH: 15
<212> TYPE: PRT
<213> ORGANISM: Human Immunodeficiency Virus (HIV-1)

<400> SEQUENCE: 7

Asp Trp His Leu Gly Gln Gly Val Ser Ile Glu Trp Arg Lys Lys
1               5                   10                  15

<210> SEQ ID NO 8
<211> LENGTH: 8
<212> TYPE: PRT
<213> ORGANISM: Human Immunodeficiency Virus (HIV-1)

<400> SEQUENCE: 8

Val Ser Ile Glu Trp Arg Lys Lys
1               5

<210> SEQ ID NO 9
<211> LENGTH: 12
<212> TYPE: PRT
<213> ORGANISM: Human Immunodeficiency Virus (HIV-1)

<400> SEQUENCE: 9

Cys Glu Trp Arg Lys Lys Arg Tyr Ser Thr Gln Val
1               5                   10

<210> SEQ ID NO 10
<211> LENGTH: 12
<212> TYPE: PRT
<213> ORGANISM: Human Immunodeficiency Virus (HIV-1)

<400> SEQUENCE: 10

Cys Glu Trp Arg Leu Lys Arg Tyr Ser Thr Gln Val
1               5                   10

<210> SEQ ID NO 11
<211> LENGTH: 8
<212> TYPE: PRT
<213> ORGANISM: Human Immunodeficiency Virus (HIV-1)

<400> SEQUENCE: 11

Glu Trp Arg Lys Lys Arg Tyr Ser
1               5

<210> SEQ ID NO 12
<211> LENGTH: 8
<212> TYPE: PRT
<213> ORGANISM: Human Immunodeficiency Virus (HIV-1)

<400> SEQUENCE: 12

Pro Lys Lys Lys Arg Lys Val Cys
1               5

<210> SEQ ID NO 13
<211> LENGTH: 9
<212> TYPE: PRT
<213> ORGANISM: Human Immunodeficiency Virus (HIV-1)

<400> SEQUENCE: 13

Cys Gly Pro Lys Asn Lys Arg Lys Val
1               5

```
<210> SEQ ID NO 14
<211> LENGTH: 9
<212> TYPE: PRT
<213> ORGANISM: Human Immunodeficiency Virus (HIV-1)

<400> SEQUENCE: 14

Cys Val Lys Arg Lys Lys Lys Pro Gly
 1               5

<210> SEQ ID NO 15
<211> LENGTH: 10
<212> TYPE: PRT
<213> ORGANISM: Human Immunodeficiency Virus (HIV-1)

<400> SEQUENCE: 15

Cys Gly Lys Lys Lys Tyr Lys Leu Lys His
 1               5                  10

<210> SEQ ID NO 16
<211> LENGTH: 15
<212> TYPE: PRT
<213> ORGANISM: Human Immunodeficiency Virus (HIV-1)

<400> SEQUENCE: 16

Cys Gly Arg Lys Lys Arg Arg Gln Arg Arg Arg Ala His Gln Asn
 1               5                  10                  15

<210> SEQ ID NO 17
<211> LENGTH: 18
<212> TYPE: PRT
<213> ORGANISM: Human Immunodeficiency Virus (HIV-1)

<400> SEQUENCE: 17

Cys Arg Gln Ala Arg Arg Asn Arg Arg Arg Arg Trp Arg Glu Arg Gln
 1               5                  10                  15

Arg Gln

<210> SEQ ID NO 18
<211> LENGTH: 17
<212> TYPE: PRT
<213> ORGANISM: Human Immunodeficiency Virus (HIV-1)

<400> SEQUENCE: 18

Cys Lys Arg Ser Met Gly Gly Trp Ser Ala Ile Arg Glu Arg Met Arg
 1               5                  10                  15

Arg

<210> SEQ ID NO 19
<211> LENGTH: 5
<212> TYPE: PRT
<213> ORGANISM: Human Immunodeficiency Virus (HIV-1)

<400> SEQUENCE: 19

Lys Lys Gln Tyr Lys
 1               5

<210> SEQ ID NO 20
<211> LENGTH: 5
<212> TYPE: PRT
<213> ORGANISM: Human Immunodeficiency Virus (HIV-1)
```

```
<400> SEQUENCE: 20

Lys Lys Lys Tyr Lys
 1               5
```